United States Patent
Goralski et al.

[11] Patent Number: 5,959,111
[45] Date of Patent: Sep. 28, 1999

[54] PROCESS FOR PREPARING 6-0-MONOESTERS OF CASTANOSPERMINE

[75] Inventors: Christian T. Goralski; Sandra K Stolz-Dunn; James E. Hitt, all of Midland; David H. Louks; Brian D. Scherzer, both of Saginaw; Mark A. Nitz, Sanford, all of Mich.

[73] Assignee: Hoechst Marion Roussel, Inc., Bridgewater, N.J.

[21] Appl. No.: 09/079,331

[22] Filed: May 14, 1998

Related U.S. Application Data

[60] Provisional application No. 60/073,236, May 22, 1997.

[51] Int. Cl.$^6$ ................................................. C07D 471/04
[52] U.S. Cl. ............................................................ 546/183
[58] Field of Search ............................................ 546/183

[56] References Cited

U.S. PATENT DOCUMENTS

| | | | |
|---|---|---|---|
| 4,952,585 | 8/1990 | Sunkara et al. | 514/299 |
| 5,004,746 | 4/1991 | Liu et al. | 514/299 |
| 5,017,563 | 5/1991 | Liu et al. | 514/299 |
| 5,385,911 | 1/1995 | Sunkara et al. | 514/299 |

OTHER PUBLICATIONS

P.S.Liu, et al., Tetrahedron Letters, vol.31,No.20, pp. 2829–2832 (1990).
R.H. Furneaux, et al., Tetrahedron vol. 50, No. 7, pp. 2131–2160 (1994).
S.David, et al., Tetrahedron vol. 41, No. 4, pp. 643–663 (1985).
W.K. Anderson, et al., Tetrahedron Letters, vol. 31, No. 2, pp. 169–170 (1990).

*Primary Examiner*—Bernard Dentz
*Attorney, Agent, or Firm*—Balaram Gupta

[57] ABSTRACT

The present invention relates to a process for preparing a compound of formula (I):

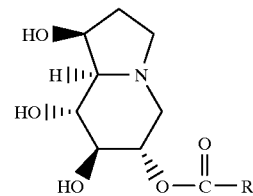

formula I wherein R is $C_1$–$C_{10}$ alkyl, phenyl or substituted phenyl, comprising treating a compound of formula (II):

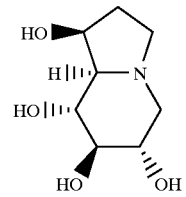

formula II with bis(tributyltin) oxide in an organic solvent selected from the group consisting of o-xylene, m-xylene, p-xylene and mixed xylenes;
and subsequently treating the reaction mixture with a compound of formula (III):

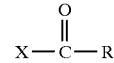

formula III wherein X is halogen and R is defined as above.

12 Claims, No Drawings

PROCESS FOR PREPARING 6-0-MONOESTERS OF CASTANOSPERMINE

This application claims the priority of U.S. Provisional Application Ser. No. 60/073,236, filed May 22, 1997.

Castanospermine, [1S-(1α,6β,7α,8β,8aβ)]-octahydro-1,6,7,8-indolizinetetrol, is an indolizidine alkaloid with the following structure:

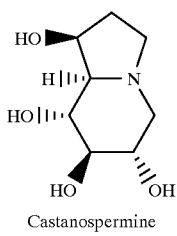

Castanospermine

It is isolated from *Castanospermum australe* as described by L. D. Hohenshutz, et al., *Phytochemistry*, 20, 811 (1981) and from *Alexa leiopetala* as described by R. J. Nash, et al., *Phytochemistry*, 27, 1403 (1988). Certain esters of castanospermine have been found to be useful in the treatment of various retroviral infections, diabetes and in the inhibition of tumor metastasis as disclosed respectively in U.S. Pat. No. 5,004,746 issued Apr. 2, 1991, U.S. Pat. No. 5,017,563 issued May 21, 1991 and U.S. Pat. No. 4,952,585 issued Aug. 28, 1990, the disclosures of which are incorporated herein by reference. More specifically, 6-O-butyrylcastanospermine.HCl, which has the following structure:

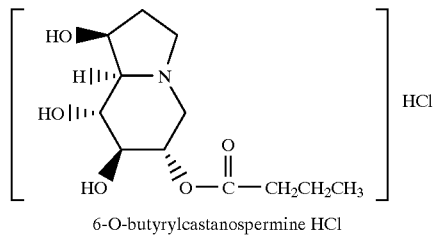

6-O-butyrylcastanospermine HCl has been of particular interest.

Interest in developing a short and efficient synthesis of the 6-O-monoesters of castanospermine has been substantial. However, with four relatively similar secondary alcohols present on castanospermine, selective mono-acylation at the 6-position has presented a significant challenge. The original synthesis of the 6-O-monoesters of castanospermine, as disclosed by Sunkara and Liu in U.S. Pat. No. 4,952,585, involved treating castanospermine with an excess of an acid chloride in pyridine at 0° C. followed by three days of stirring. An aqueous extraction followed by purification of the complex mixture by radial chromatography provided the 6-O-monoester in poor yield.

A subsequent synthesis of the 6-O-monoesters of castanospermine, disclosed by P. S. Liu, et al. *Tetrahedron Lett.*, 31(20), 2829 (1990), utilized selective protection and deprotection of the hydroxyl groups with mono-acylation of the 6-hydroxyl group. The overall process resulted in improved yields, however a total of five steps was required starting from castanospermine.

A one-pot procedure for the preparation of 6-monoesters of castanospermine was reported by W. K. Anderson, et al., *Tetrahedron Lett.* 31(2), 169 (1990) wherein castanospermine was treated with dibutyltin oxide in methanol. The reaction was heated to reflux, then cooled and treated with an acid chloride and triethylamine to provide the desired free base of the 6-monoester of castanospermine in yields ranging from 18% to 44% after flash chromatography.

An improved one-pot procedure for the preparation of 6-monoesters of castanospermine was reported by P. C. Tyler, et al., *Tetrahedron*, 50(7), 2131 (1994) wherein castanospermine was treated with bis(tributyltin) oxide in toluene. The reaction was heated to reflux with removal of water in order to drive the reaction to completion. After about 2 hours, the reaction was cooled to −10° C. and treated with an acid chloride to provide the desired 6-monoester of castanospermine. Using this procedure, the free bases of 6-O-benzoylcastanospermine and 6-O-butyrylcastanospermine were prepared in yields of 94% and 83%, respectively.

However, it has been found that as the size of the reaction is increased following the procedure of Tyer et al., the time required to drive the formation of the tributyltin ether to completion through removal of water is also increased. It has further been found that by replacing toluene with xylene as the solvent in the process of Tyler et al., the time required to drive the reaction to completion by removal of water is substantially decreased.

SUMMARY OF THE INVENTION

The present invention relates to a process for preparing a compound of formula (I):

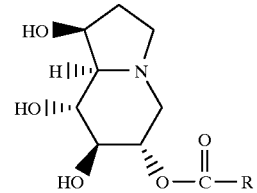

formula I wherein R is $C_1$–$C_{10}$ alkyl, phenyl or substituted phenyl, comprising treating a compound of formula (II):

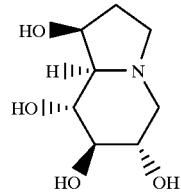

formula II with bis(tributyltin) oxide in an organic solvent selected from the group consisting of o-xylene, m-xylene, p-xylene and mixed xylenes;

and subsequently treating the reaction mixture with a compound of formula (III):

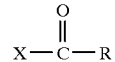

formula III wherein X is halogen and R is defined as above.

The invention further relates to a process for preparing a compound of formula (IV):

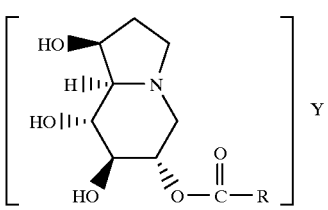

formula IV wherein R is $C_1$–$C_{10}$ alkyl, phenyl or substituted phenyl; and Y is an acid selected from the group consisting of hydrogen bromide, hydrogen chloride, sulfuric acid, phosphoric acid, nitric acid, formic acid, acetic acid, propionic acid, succinic acid, glycolic acid, lactic acid, malic acid, tartaric acid, citric acid, ascorbic acid, α-ketoglutaric acid, glutamic acid, aspartic acid, maleic acid, hydroxymaleic acid, pyruvic acid, phenylacetic acid, benzoic acid, p-aminobenzoic acid, anthranilic acid, p-hydroxybenzoic acid, salicyclic acid, hydroxyethanesulfonic acid, ethylenesulfonic acid, halobenzenesulfonic acid, toluenesulfonic acid, naphthalenesulfonic acid, methanesulfonic acid and sulfanilic acid, comprising;

a) treating a compound of formula (II):

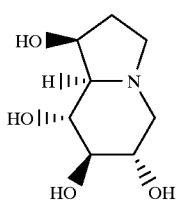

formula II with bis(tributyltin) oxide in an organic solvent selected from the group consisting of o-xylene, m-xylene, p-xylene and mixed xylenes;
and subsequently treating the reaction mixture with a compound of formula (III):

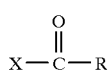

formula III wherein X is halogen and R is defined as above; and b) subsequently treating the reaction mixture with a suitable organic solvent and an acid of formula Y defined above.

DETAILED DESCRIPTION OF THE INVENTION

As used herein the term "$C_1$–$C_4$ alkyl" refers to a saturated straight or branched chain alkyl radical of one to four carbon atoms. Included within the scope of this term are methyl, ethyl, n-propyl, isopropyl, n-butyl, isobutyl and the like. The term "$C_1$–$C_6$ alkyl" refers to a branched or straight chained, or cyclic alkyl radical containing from 1–6 carbon atoms, such as methyl, ethyl, n-propyl, isopropyl, n-butyl, isobutyl, t-butyl, n-pentyl, cyclopentyl, n-hexyl, cyclohexyl, and the like. The term "$C_1$–$C_{10}$ alkyl" refers to a saturated straight or branched chain or cyclic alkyl radical of one to ten carbon atoms, including methyl, ethyl, propyl, isopropyl, n-butyl, isobutyl, t-butyl, n-pentyl, isopentyl, hexyl, 2,3-dimethyl-2-butyl, heptyl, 2,2-dimethyl-3-pentyl, 2-methyl-2-hexyl, octyl, 4-methyl-3-heptyl, nonyl, decyl and the like.

The term "phenyl" refers the phenyl functionality of the formula:

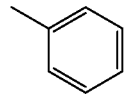

The term "substituted phenyl" refers the substituted phenyl functionality of the formula:

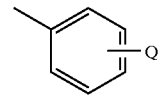

wherein Q is a $C_1$–$C_4$ alkyl, nitro or halo which can be located at the ortho, meta or para position on the ring.

The terms "halo", "halogen" or "halide" refers to a fluorine, chlorine, bromine or iodine atom.

As used herein the term "ethanol 3C" refers to ethanol which has been denatured with 5% isopropanol.

The term "pharmaceutically acceptable salt" refers to those salts that are not substantially toxic at the dosage administered to achieve the desired effect and do not independently possess significant pharmacological activity. The salts included within the scope of this term are hydrobromide, hydrochloride, sulfuric, phosphoric, nitric, formic, acetic, propionic, succinic, glycolic, lactic, malic, tartaric, citric, ascorbic, α-ketoglutaric, glutamic, aspartic, maleic, hydroxymaleic, pyruvic, phenylacetic, benzoic, p-aminobenzoic, anthranilic, p-hydroxybenzoic, salicyclic, hydroxyethanesulfonic, ethylenesulfonic, halobenzenesulfonic, toluenesulfonic, naphthalenesulfonic, methanesulfonic, sulfanilic, and the like. Such salts can exist in either a hydrated or substantially anhydrous form.

The pharmaceutically acceptable salts of formula (I) are prepared from the corresponding acids disclosed immediately above, such as hydrogen bromide, hydrogen chloride, sulfuric acid, phosphoric acid, nitric acid, formic acid, acetic acid, propionic acid, succinic acid, glycolic acid, lactic acid, malic acid, tartaric acid, citric acid, ascorbic acid, α-ketoglutaric acid, glutamic acid, aspartic acid, maleic acid, hydroxymaleic acid, pyruvic acid, phenylacetic acid, benzoic acid, p-aminobenzoic acid, anthranilic acid, p-hydroxybenzoic acid, salicyclic acid, hydroxyethanesulfonic acid, ethylenesulfonic acid, halobenzenesulfonic acid, toluenesulfonic acid, naphthalenesulfonic acid, methanesulfonic acid, sulfanilic acid and the like. The preferred suitable acid is hydrogen chloride.

The compounds of formula (I) and (IV) can be prepared as described in Scheme I. All substituents, unless otherwise indicated, are previously defined. The reagents and starting materials are readily available to one of ordinary skill in the art.

Scheme I

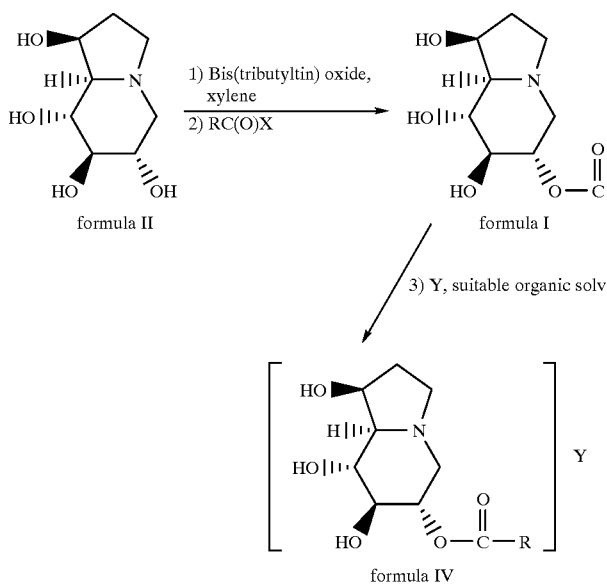

In Scheme I, step 1, under an inert atmosphere, such as nitrogen, castanospermine (formula II) is combined with a suitable organic solvent selected from the group consisting of o-xylene, m-xylene, p-xylene and mixed xylenes, and about 1.5 to about 2.5 equivalents of bis(tributyltin) oxide, with about 2.2 equivalents of bis(tributyltin) oxide being preferred. The mixture is heated at reflux, and, the by-product water is collected via a suitable apparatus, such as a Dean-Stark trap in order to drive the reaction to completion. The mixture is heated at reflux for about 0.5 to about 6 hours, with about 1 to about 2 hours being preferred. In step 2 of Scheme I, the mixture is then cooled to about −20° C. to about −10° C. with about −15° C. being preferred. To the cooled mixture is added about 1.5 to about 2.0 equivalents of an acid chloride of formula III, with about 1.8 equivalents being preferred.

formula III

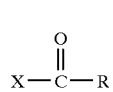

The acid chloride of formula III is added at such a rate that the temperature of the mixture is maintained between about −20° C. to about 20° C., with about −17° C. to about 5° C. being preferred. Examples of acid chlorides of formula III include acetyl chloride, propionyl chloride, butyryl chloride, isobutyryl chloride, trimethylacetyl chloride, valeryl chloride, isovaleryl chloride, tert-butylacetyl chloride, hexanoyl chloride, heptanoyl chloride, 2-ethylhexanoyl chloride, octanoyl chloride, nonanoyl chloride, decanoyl chloride, benzoyl chloride, 4-butylbenzoyl chloride, p-tert-butylbenzoyl chloride, o-, m- or p-chlorobenzoyl chloride, m- or p-nitrobenzoyl chloride, o-, m- or p-toluoyl chloride and the like. Butyryl chloride is the preferred acid chloride of formula III. After addition of the acid chloride is complete, the mixture is allowed to warm to about 20° C. and is then diluted with a suitable organic solvent, such as ethanol 3C (ethanol denatured with 5% isopropanol). Isolation of the free base of formula I from the reaction mixture is somewhat difficult, thus it is preferred that the compound of formula I be directly converted to the compound of formula IV without intermediate isolation of the compound of formula I, by treatment with an acid of formula Y, which has been defined previously herein. For example, in step 3 of Scheme I, the compound of formula I in the suitable organic solvent, such as a mixture of xylenes and ethanol 3C, is made strongly acidic by treatment with an acid of formula Y, such as anhydrous hydrogen chloride. The resulting compound of formula IV is isolated and purified by techniques well known by one of ordinary skill in the art, such as crystallization. For example, the solution may be seeded with several crystals of the desired compound of formula IV in order to initiate crystallization. The resulting slurry is then cooled with an ice bath and the solids are collected by filtration, for example through a centrifugal filter. The solids are then washed with a suitable organic solvent, such as heptanes, to remove residual tributyltin compounds, and air and vacuum dried to provide the compound of formula IV.

The following examples present typical syntheses as described in Scheme I. These examples are understood to be illustrative only and are not intended to limit the scope of the present invention in any way. It is further understood that the apparatus necessary for carrying out the precent invention on the chosen scale is readily determined by one of ordinary skill in the art, with the following exception. The removal of the by-product water in step 1 of Scheme I may necessarily be enhanced as the size of the reaction is increased. This can be accomplished by the use of a rectification column during reflux, by increasing the heat transfer area available during reflux, by sparging an inert gas, such as nitrogen, through the refluxing solution, by sparging vapor phase solvent through the refluxing solution, by sending back solvent to the refluxing solution that has a water content much less than the saturation level, using a technique such as drying with a drying agent, or by other methods that will shift the equilibrium of the desired reaction to favor the desired product via removal of water from the reaction solution.

As used herein, the following terms have the indicated meanings: "kg" refers to kilograms; "m²/g" refers to square meters per gram and is used as a measurement of particle surface area; "lbs" refers to pounds; "g" refers to grams; "mg" refers to milligrams; "μg" refers to micrograms; "ppm" refers to parts per million; "mmol" refers to millimoles; "mL" refers to milliliters; "cm" refers to centimeters; "L" refers to liters; "° C." refers to degrees Celsius; "° F." refers to degrees Fahrenheit; "mm Hg" refers to millimeters of mercury; "rpm" refers to revolutions per minute; "$R_f$" refers to retention factor; "bp" refers to boiling point; "mp" refers to melting point; "dec" refers to decomposition; "M" refers to molar; "mM" refers to millimolar; "μM" refers to micromolar; "nM" refers to nanomolar; "μL" refers to microliters; "HPLC" refers to high performance liquid chromatography; "eq" refers to equivalents; "h" refers to hours; "N" refers to normal; and "$R_t$" refers to retention time.

EXAMPLE 1

General Procedure for Preparing 6-O-Butyrylcastanospermine [1S-(1α,6β,7α,8β,8aβ)]-octahydro-1,6,7,8-indolizinetetrol 6-butanoate HCl, Two Liter Scale, with Xylene as Solvent

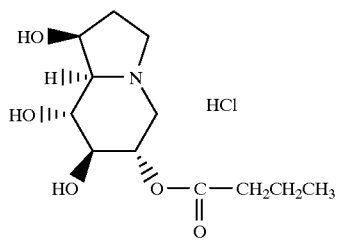

Scheme I, step 1; A 2 liter, three-neck flask equipped with a mechanical stirrer, thermometer and a Dean-Stark trap fitted with a condenser bearing a nitrogen bubbler is charged with castanospermine (20.00 g, 0.106 mol), bis(tributyltin) oxide (115 mL) and xylene (600 mL, mixed isomer,). The mixture is heated to reflux and water is collected in the Dean-Stark trap. After 20 minutes, the reaction mixture becomes homogeneous and after one hour and 5 minutes the heating is stopped. Approximately 2 mL of water is collected. The reaction is allowed to cool to room temperature.

Scheme I, step 2; The Dean-Stark trap is removed from the above reaction and is replaced with a Claisen adapter fitted with a nitrogen bubbler and a pressure equalizing addition funnel. The reaction mixture is cooled to −17° C. and butyryl chloride (20.20 g, 0.190 mol) is added slowly over 10 minutes, maintaining the temperature between −17° C. and −5° C. The reaction mixture is then allowed to warm to 20° C.

Scheme I, step 3; The above reaction mixture is diluted with ethanol 3C (600 mL, ethanol denatured with 5% isopropanol) and treated with anhydrous hydrogen chloride (14.13 g). The reaction temperature rises from 20° C. to 32° C. during the hydrogen chloride addition. The reaction mixture is seeded with several crystals of 6-O-butyrylcastanospermine hydrochloride to produce a slurry of a white solid. The slurry is allowed to stir at room temperature overnight and then is cooled with an ice bath and stirred for 2 hours. The white solid is collected by filtration, air dried, washed with heptane (100 mL, mixed isomers), air dried for 2 hours and dried under vacuum at room temperature for 2 hours to provide the title compound (25.14 g, 80.2%).

TABLE I

Results of 11 Experiments for Preparing 6-O-Butyrylcastanospermine HCl in Xylene Following the General Procedure Described in Example 1.

| Castano-spermine g | BTBTO[1] (mL), g | Xylene mL, (g) | Reaction Time hours | Yield % | Castano-spermine % |
|---|---|---|---|---|---|
| 20.00 | (115) | 600 | 1.1 | 80.2 | 0.56 |
| 40.00 | (230) | 525 | 1.5 | 81.5 | 0.42 |
| 20.00 | (54) | 600 | 2.0 | 47.5 | — |
| 20.00 | (81) | 600 | 2.5 | 77.7 | 0.51 |
| 20.00 | (94.5) | 600 | 2.0 | 79.4 | 0.44 |
| 20.00 | (81) | 600 | 2.75 | 69.6 | — |
| 20.00 | (95) | 600 | 2.0 | 74.0 | 1.44 |
| 20.25 | 137.7 | (222.7) | 2.0 | 66.8 | 0.54 |
| 20.25 | 137.7 | (222.7) | 2.0 | 69.5 | 1.03 |
| 20.25 | 137.7 | (222.7) | 2.0 | 69.3 | 1.06 |
| 20.00 | 132.3 | (522.3) | 2.0 | 77.4 | 0.40 |

[1]BTBTO refers to bis(tributyltin) oxide.

EXAMPLE 2

General Procedure for Preparing 6-O-Butyrylcastanospermine [1S-(1α,6β,7α,8β,8aβ)]-octahydro-1,6,7,8-indolizinetetrol 6-butanoate HCl, Two Liter Scale with Toluene as Solvent Scheme I, step 1; A 2 liter, three-neck flask equipped with a mechanical stirrer, thermometer and a Dean-Stark trap fitted with a condenser bearing a nitrogen bubbler is charged with castanospermine (20.00 g, 0.106 mol), bis(tributyltin) oxide (115 mL) and toluene (600 mL). The mixture is heated to reflux and water is collected in the Dean-Stark trap. After 3.33 hours the heating is stopped and the reaction mixture is cooled to 20° C.

Scheme I, step 2; The Dean-Stark trap is removed from the above reaction and is replaced with a Claisen adapter fitted with a nitrogen bubbler and a pressure equalizing addition funnel. The reaction mixture is cooled to −13° C. and butyryl chloride (20.20 g, 0.190 mol) is added slowly over 10 minutes, maintaining the temperature between −13° C. and −8° C. The reaction mixture is then allowed to warm to room temperature.

Scheme I, step 3; The above reaction mixture is diluted with ethanol 3C (650 mL, ethanol denatured with 5% isopropanol) and treated with anhydrous hydrogen chloride (approximately 18.00 g, 0.494 mol). The reaction temperature rises from 18° C. to 30° C. during the hydrogen chloride addition. The reaction mixture is seeded with several crystals of 6-O-butyrylcastanospermine hydrochloride to produce a slurry of a white solid. The slurry is allowed to stir at room temperature overnight and then is cooled with an ice bath and stirred for 2 hours. The white solid is collected by filtration, air dried, washed with heptane (100 mL, mixed isomers), air dried and dried under vacuum at room temperature to provide the title compound (24.26 g, 77.4%).

EXAMPLE 3

General Procedure for Preparing 6-O-Butyrylcastanospermine [1S-(1α,6β,7α,8β,8aβ)]-octahydro-1,6,7,8-indolizinetetrol 6-butanoate HCl, Pilot Plant Scale, with Xylene as Solvent Scheme I, step 1; A 200 gallon batch reactor fitted with a Dean-Stark trap is charged with bis(tributyltin) oxide (326 lbs), mixed xylenes (528 lbs) and castanospermine (48 lbs)

with an agitator speed of about 60 rpm and jacket temperature set at 25° C. The condenser temperature is set at 10° C. and the mixture is then heated by increasing the jacket temperature of the reactor at a rate of 5° C./min up to reflux temperature of 175° C. After 6 hours, 70 lbs of xylene/water are collected from the trap. The condenser is then set at −25° C. and after 1.5 hours, 45 lbs of xylene/water are collected from the trap. The reaction is then cooled to about 25° C.

The progress of the above stannylation reaction is evaluated by the following procedure; A 1.7 g sample of the above reaction mixture is transferred to a clean, dry, 7-dram vial. To this is added benzoyl chloride (0.14–0.16 g), the vial is sealed and the reaction mixture is shaken. A precipitate of the benzoyl derivative of castanospermine (6-O-benzoylcastanospermine) quickly forms. The vial is then nearly filled with water, adjusted to pH 2.0 with phosphoric acid, a small amount of mixed heptanes is added, and the mixture is vigorously shaken. The layers are then allowed to separate. Two disposable pipette volumes of the aqueous layer are transferred to a clean, 7-dram vial and the vial is nearly filled with pH 2.0 water. The mixture is shaken and the resulting solution is analyzed by High Performance Liquid Chromatography under standard conditions readily determined by one of ordinary skill in the art to determine whether the reaction has gone to completion.

Scheme I, step 2; The reaction mixture is then cooled by setting the jacket temperature of the reactor at −15° C., and with the agitator speed still at about 60 rpm, butyryl chloride (48 lbs) is added at such a rate that the reaction temperature is maintained below 10° C. After one hour the jacket temperature is set at 25° C. and the reaction mixture is stirred for an additional hour.

Scheme I, step 3; The reaction mixture is then filtered through a 0.2 micron retention polypropylene filter into a 300 gallon reactor to which a solution of ethanol 3C (384 lbs) and anhydrous HCl (16.5 lbs bubbled into the ethanol 3C) has already been charged. The original 200 gallon reactor and transfer line are flushed with mixed xylenes (123 lbs) into the 300 gallon reactor. The agitator speed is set at about 30 rpm and the jacket temperature is set at 25° C. Anhydrous HCl (12 lbs) is then bubbled into the reaction mixture until a pH of less then 3.0 is obtained (4 hours). The jacket temperature is then set at −10° C. and the mixture is stirred for 4 hours. The title compound is then isolated by centrifugation and the product is washed with mixed heptanes (192 lbs). The title compound is dried under vacuum (100 mmHg) at a temperature of less than 35° C. to provide the dry title compound.

TABLE II

Results of 21 Experiments for Preparing
6-O-Butyrylcastanospermine HCl in Xylene Following
the General Procedure Described in Example 3.

| Castanospermine lbs | BTBTO[1] lbs | BuCl[2] lbs | Xylene lbs | Yield[3] lbs | Yield[3] % |
|---|---|---|---|---|---|
| 30.0 | 204.0 | 30.0 | 330.0 | 34.8 | 74.1 |
| 40.0 | 272.0 | 40.0 | 442.0 | 53.1 | 85.0 |
| 49.5 | 333.5 | 49.0 | 609.0 | 66.0 | 85.3 |
| 50.5 | 341.0 | 50.0 | 550.0 | 57.3 | 72.6 |
| 40.0 | 272.2 | 40.0 | 440.3 | 39.2 | 62.7 |
| 48.0 | 326.0 | 48.0 | 528.0 | 65.3 | 87.1 |
| 48.0 | 326.0 | 48.0 | 528.0 | 61.0 | 81.3 |
| 48.0 | 326.0 | 48.0 | 528.0 | 56.8 | 75.8 |
| 47.7 | 320.7 | 47.0 | 517.1 | 60.5 | 81.1 |
| 52.0 | 354.4 | 52.0 | 572.0 | 68.9 | 84.8 |
| 52.6 | 354.5 | 52.0 | 572.5 | 61.9 | 75.3 |

TABLE II-continued

Results of 21 Experiments for Preparing
6-O-Butyrylcastanospermine HCl in Xylene Following
the General Procedure Described in Example 3.

| Castanospermine lbs | BTBTO[1] lbs | BuCl[2] lbs | Xylene lbs | Yield[3] lbs | Yield[3] % |
|---|---|---|---|---|---|
| 51.3 | 362.4 | 52.0 | 572.5 | 71.9 | 89.7 |
| 37.5 | 255.5 | 37.5 | 532.0 | 50.3 | 85.8 |
| 37.2 | 255.0 | 37.5 | 412.5 | 46.7 | 80.4 |
| 48.0 | 326.3 | 48.0 | 529.9 | 53.3 | 71.1 |
| 52.0 | 326.9 | 48.0 | 528.1 | 56.7 | 69.8 |
| 48.0 | 327.0 | 48.0 | 528.0 | 63.0 | 84.0 |
| 48.1 | 326.5 | 48.0 | 528.0 | 59.4 | 79.0 |
| 47.8 | 326.5 | 48.0 | 528.0 | 66.2 | 88.5 |
| 55.0 | 374.7 | 55.0 | 605.7 | 69.7 | 81.1 |
| 55.0 | 374.0 | 55.0 | 605.0 | 81.5 | 94.8 |

[1]BTBTO refers to bis(tributyltin) oxide.
[2]BuCl refers to butyryl chloride.
[3]Yield of 6-O-butyrylcastanospermine HCl Purification of 6-O-butyrylcastanospermine HCl.

Load ethanol 3C and water in a ratio of 95/5 v/v into a 200 gallon glass-lined steel vessel (RC-1). Then load the above prepared 6-O-butyrylcastanospermine HCl wetcake into RC-1 until the mixture is 13 % by weight 6-O-butyrylcastanospermine HCl. Pressure test the vessel using nitrogen and set the agitator speed at 80 rpm. Preheat the jacket of a 300 gallon glass-lined steel vessel (RC-2) to 75° C. Then heat the contents of RC-1 to reflux and hold at reflux for 10 minutes. Pressure transfer the solution from RC-1 to RC-2 through a cartridge filter to remove any extraneous particulate matter. Set the agitator of RC-2 at 30 rpm and the jacket of RC-2 to 70° C. With the internal temperature of RC-2 at >72° C., briefly increase the agitator to approximately 120 rpm several times to dissolve any rind present on the reactor wall. Then set the RC-2 jacket to control at 10° C. below the internal temperature. When the internal temperature of RC-2 reaches about 56° C., set the RC-2 jacket at 55° C. When the RC-2 internal temperature reaches a steady state at approximately 54° C., seed the contents of RC-2 by loading a slurry of polish filtered ethanol 3C and previously crystallized 6-O-butyrylcastanospermine HCl. When it has been determined that the slurry of crystals has reached steady state (approximately 3 hours), increase the internal temperature of RC-2 to reduce the mass of crystals by about 70–80% (approximately 64° C.). Maintain this temperature for about 2 hours and then initiate a suitable cooling profile of RC-2 as described in Table III below.

TABLE III

Cooling Profile of the Jacket.

| | Target Temperature ° C. | Rate of Cooling, ° C./hour |
|---|---|---|
| Cool from current jacket temperature to; | 48 | 1.1 |
| Cool from 48° C. to; | 30 | 2.2 |
| Cool from 30° C. to; | 5 | 5.5 |
| Cool from 5° C. to; | −10 | 11 |

When the internal temperature of RC-2 is less than 0° C., hold the reactor contents at this temperature for 2 hours. Then pressure transfer the contents of RC-2 to a 30 inch diameter stainless steel centrifuge (CC-1) to isolate the purified 6-O-butyrylcastanospermine HCl. Use a 1–3 or a 3–8 micron rated centrifuge bag and rotate the centrifuge basket at approximately 400 rpm. Wash the wetcake in CC-1 with chilled ethanol 3C (unit ratio=0.8, with crude product as the basis) that has been polish filtered. Set the centrifuge basket to rotate at 1000 rpm and deliquor the wetcake for approximately 1 hour. Then unload the wetcake from CC-1 to double-lined fiber packs with desiccant bags placed in between the liners on the bottom and top of the fiberpack.

What is claimed is:

1. A process for preparing a compound of the formula:

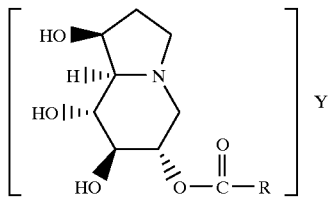

wherein R is $C_1$–$C_{10}$ alkyl, phenyl or substituted phenyl; and Y is an acid selected from the group consisting of hydrogen bromide, hydrogen chloride, sulfuric acid, phosphoric acid, nitric acid, formic acid, acetic acid, propionic acid, succinic acid, glycolic acid, lactic acid, malic acid, tartaric acid, citric acid, ascorbic acid, α-ketoglutaric acid, glutamic acid, aspartic acid, maleic acid, hydroxymaleic acid, pyruvic acid, phenylacetic acid, benzoic acid, p-aminobenzoic acid, anthranilic acid, p-hydroxybenzoic acid, salicyclic acid, hydroxyethanesulfonic acid, ethylenesulfonic acid, halobenzenesulfonic acid, toluenesulfonic acid, naphthalenesulfonic acid, methanesulfonic acid and sulfanilic acid, comprising;

a) treating a compound of the formula:

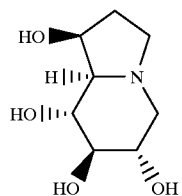

with bis(tributyltin) oxide in an organic solvent selected from the group consisting of o-xylene, m-xylene, p-xylene and mixed xylenes;
and subsequently treating the reaction mixture with a compound of the formula:

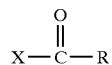

wherein X is halogen and R is defined as above; and
b) subsequently treating the reaction mixture with a suitable organic solvent and an acid of formula Y defined above.

2. The process according to claim 1 wherein R is $C_1$–$C_4$ alkyl or phenyl.

3. The process according to claim 1 wherein R is —$CH_2CH_2CH_3$.

4. The process according to claim 3 wherein the organic solvent is mixed xylenes.

5. The process according to claim 4 wherein Y is hydrogen chloride.

6. The process according to claim 5 wherein X is Cl.

7. The process according to claim 6 wherein the mixture comprising the compound of said formula,

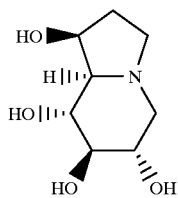

said bis(tributyltin)oxide and said mixed xylenes, is heated at reflux for about 1 to about 6 hours.

8. The process according to claim 7 wherein the mixture is heated at reflux for about 1 to about 2 hours.

9. The process according to claim 8 wherein the suitable organic solvent is ethanol 3C.

10. A process for purifying a compound of the formula:

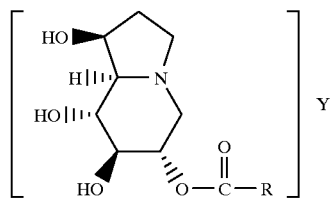

wherein R is $C_1$–$C_{10}$ alkyl, phenyl or substituted phenyl; and Y is an acid selected from the group consisting of hydrogen bromide, hydrogen chloride, sulfuric acid, phosphoric acid, nitric acid, formic acid, acetic acid, propionic acid, succinic acid, glycolic acid, lactic acid, malic acid, tartaric acid, citric acid, ascorbic acid, α-ketoglutaric acid, glutamic acid, aspartic acid, maleic acid, hydroxymaleic acid, pyruvic acid, phenylacetic acid, benzoic acid, p-aminobenzoic acid, anthranilic acid, p-hydroxybenzoic acid, salicyclic acid, hydroxyethanesulfornic acid, ethylenesulfonic acid, halobenzenesulfonic acid, toluenesulfonic acid, naphthalenesulfonic acid, methanesulfonic acid and sulfanilic acid, comprising;

a) combining above said compound with about a 95/5 v/v solution of ethanol and water to provide about a 13% by weight solution of said compound;
b) heating the solution at reflux with agitation;
c) cooling the solution to about 54° C.;
d) seeding the solution with said compound to produce a crystal slurry;
e) heating the crystal slurry at about 64° C. until the crystal slurry is reduced by about 70% to about 80%;
f) maintaining the temperature of the crystal slurry at about 64° C. for about 2 hours;
g) initiating a suitable cooling profile to provide a final temperature of the crystal slurry of less than about 0° C.;
h) collecting the purified compound.

11. The process according to claim 10 wherein R is —$CH_2CH_2CH_3$.

12. The process according to claim 11 wherein Y is HCl.

* * * * *

UNITED STATES PATENT AND TRADEMARK OFFICE
CERTIFICATE OF CORRECTION

PATENT NO.   :   5,959,111

DATED        :   Sept. 28, 1999

INVENTOR(s)  :   Christian T. Goralski, et al

It is certified that error appears in the above-identified patent and that said Letters Patent is hereby corrected as shown below:

Title page, in the Inventors Section, last line, after comma, before all of Mich, should include one more inventor's name, --Mark R. Smit, Midland,--.

Column 6, Line 50 reads "precent" and should read --present--.

Signed and Sealed this

Seventeenth Day of April, 2001

*Attest:*

NICHOLAS P. GODICI

*Attesting Officer*   *Acting Director of the United States Patent and Trademark Office*